United States Patent
Pomper et al.

(10) Patent No.: US 9,498,546 B2
(45) Date of Patent: Nov. 22, 2016

(54) SYNTHESIS AND APPLICATION OF NOVEL IMAGING AGENTS CONJUGATED TO DPA 713 ANALOGS FOR IMAGING INFLAMMATION

(71) Applicant: THE JOHNS HOPKINS UNIVERSITY, Baltimore, MD (US)

(72) Inventors: Martin Gilbert Pomper, Baltimore, MD (US); Haofan Wang, Rockville, MD (US); Catherine Anne Foss, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 248 days.

(21) Appl. No.: 14/385,090

(22) PCT Filed: Mar. 14, 2013

(86) PCT No.: PCT/US2013/031461
§ 371 (c)(1),
(2) Date: Sep. 12, 2014

(87) PCT Pub. No.: WO2013/138612
PCT Pub. Date: Sep. 19, 2013

(65) Prior Publication Data
US 2015/0044141 A1 Feb. 12, 2015

Related U.S. Application Data

(60) Provisional application No. 61/610,783, filed on Mar. 14, 2012.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *C07D 487/04* | (2006.01) |
| *G01N 33/574* | (2006.01) |
| *G01N 33/58* | (2006.01) |

(52) U.S. Cl.
CPC ....... *A61K 49/0052* (2013.01); *A61K 49/0032* (2013.01); *C07D 487/04* (2013.01); *G01N 33/57492* (2013.01); *G01N 33/582* (2013.01); *A61K 49/0017* (2013.01); *A61K 2123/00* (2013.01); *G01N 2333/705* (2013.01)

(58) Field of Classification Search
None
See application file for complete search history.

(56) References Cited

FOREIGN PATENT DOCUMENTS

| WO | 2008022396 A1 | 2/2008 |
|---|---|---|
| WO | 2010020000 A1 | 2/2010 |

OTHER PUBLICATIONS

International Search Report and Written Opinion dated Aug. 30, 2013 from PCT International Application No. PCT/US2013/031461.
E.L. Crossley et al., 'Synthesis and cellular uptake of boron-rich pyrazolopyrimidines: exploitation of the translocator protein for the efficient delivery of boron into human glioma cells' Chemical Communications, vol. 47, pp. 12179-12181 (2011).
A. Reynolds et al., 'Pyrazolo[1,5-a]pyrimidine acetamides: 4-Phenyl alkyl ether derivatives as potent ligands for the 18 kDa translocator protein (TSPO)' , Bioorganic &Medicinal Chemistry Letters, vol. 20, pp. 5799-5802 (2010).
D.R.J. Owen et al., 'Mixed-Affinity Binding in Humans with 18-kDa Translocator Protein Ligands' , The Journal of Nuclear Medicine, vol. 52, pp. 24-32 (2011).

*Primary Examiner* — Michael G Hartley
*Assistant Examiner* — Melissa Perreira
(74) *Attorney, Agent, or Firm* — Ward and Smith, P.A.; Jeffrey W. Childers

(57) ABSTRACT

The present invention provides analog compounds of DPA-713 which specifically bind the translocator protein (TSPO), which is upregulated in activated leukocytes, some malignant tumors and tissues involved in steroid biogenesis. These compounds are linked via a linking moiety to a variety of imaging agents, including, for example, near infra-red dyes. The compounds of the present invention are useful for both pre-clinical near-IR fluorescence imaging (NIRF) and use in optically-guided interventions including NIRF endoscopy. Methods of use in diagnosis and treatment of TSPO related disease are also provided.

12 Claims, 9 Drawing Sheets

SYNTHESIS AND APPLICATION OF NOVEL IMAGING AGENTS CONJUGATED TO DPA 713 ANALOGS FOR IMAGING INFLAMMATION

REFERENCE TO RELATED APPLICATIONS

This application is a 35 U.S.C. 371 U.S. national phase entry of International Application No. PCT/US2013/31461 having an international filing date of Mar. 14, 2013, which claims the benefit of U.S. Provisional Application No. 61/610,383, filed on Mar. 14, 2012, which is hereby incorporated by reference for all purposes as if fully set forth herein.

STATEMENT OF GOVERNMENTAL INTEREST

This invention was made with U.S. government support under grant no. DP2 OD006492-01. The U.S. government has certain rights in the invention.

BACKGROUND OF THE INVENTION

The translocator protein (TSPO), formerly known as the peripheral benzodiazepine receptor (PBR), is an 18 kDa protein mainly found on the outer mitochondrial membrane. It has been shown to be overexpressed in CNS diseases and in certain types of cancer and has become an attractive target in imaging agent development. Several small molecule PET and SPECT ligands has been developed for TSPO imaging of PBR, such as [$^{11}$C]PK11195, Ro 5-4864, DAA1106, PBR28, AC-5216, Vinpocetine and [$^{11}$C]DPA-713.

DPA-713 is a small molecule that binds to the translocator protein (TSPO), which is upregulated in activated' leukocytes, some malignant tumors and tissues involved in steroid biogenesis.

DPA-713 is a compound from the family of pyrazolopyrimidines which is twice as potent as PK 11195 and 10 times more hydrophilic. Several radiolabeled PET and SPECT ligands has been developed, including [$^{11}$C]DPA-713, [$^{18}$F]DPA-714 and [$^{125}$I]DPA-713. Imaging studies in animal models and humans have shown promising TSPO targeting characteristics.

Presently there still exists a need for non-radioactive imaging agents which are specific for the TSPO enzyme, for diagnosis and treatment of diseases.

SUMMARY OF THE INVENTION

In accordance with an embodiment, the present invention provides a compound of formula I:

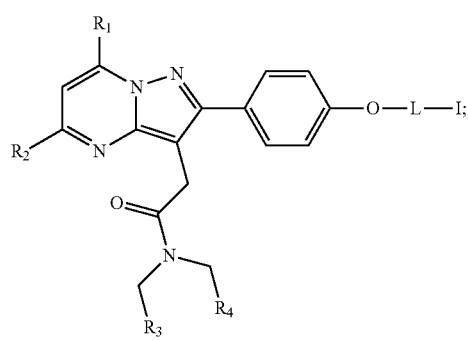

(I)

wherein $R_1$, $R_2$, $R_3$ and $R_4$ independently represent hydroxy, $C_1$ to $C_{10}$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, an amino acid residue, or a substituted amino acid residue; L is a linker of 1-10 carbon atoms; and I is an imaging agent covalently linked to the linker via an amide linkage.

In accordance with another embodiment, the present invention provides a pharmaceutical composition comprising an effective amount of a compound of formula I and a pharmaceutically acceptable carrier.

In accordance with a further embodiment, the present invention provides a method of imaging a cell or population of cells having translocator protein (TSPO) activity comprising contacting the cell or population of cells with the compound described above, in an effective amount for the compound to bind TSPO and be visualized with infra-red light.

In accordance with an embodiment, the present invention provides a method of imaging a cell or population of cells having TSPO activity in a subject comprising: a) administering to the subject an effective amount of the compound described above or the pharmaceutical composition described above; b) allowing sufficient time for the compound described above or the pharmaceutical composition described above to bind the TSPO in the cell or population of cells in the subject; c) exposing the cell or population of cells in the subject to a sufficient amount of infra-red light at the appropriate wavelength; and d) detecting the infra-red fluorescence from the cell or population of cells of the subject which bound the compound described above or the pharmaceutical composition described above.

DETAILED DESCRIPTION OF THE INVENTION

Figure 1:
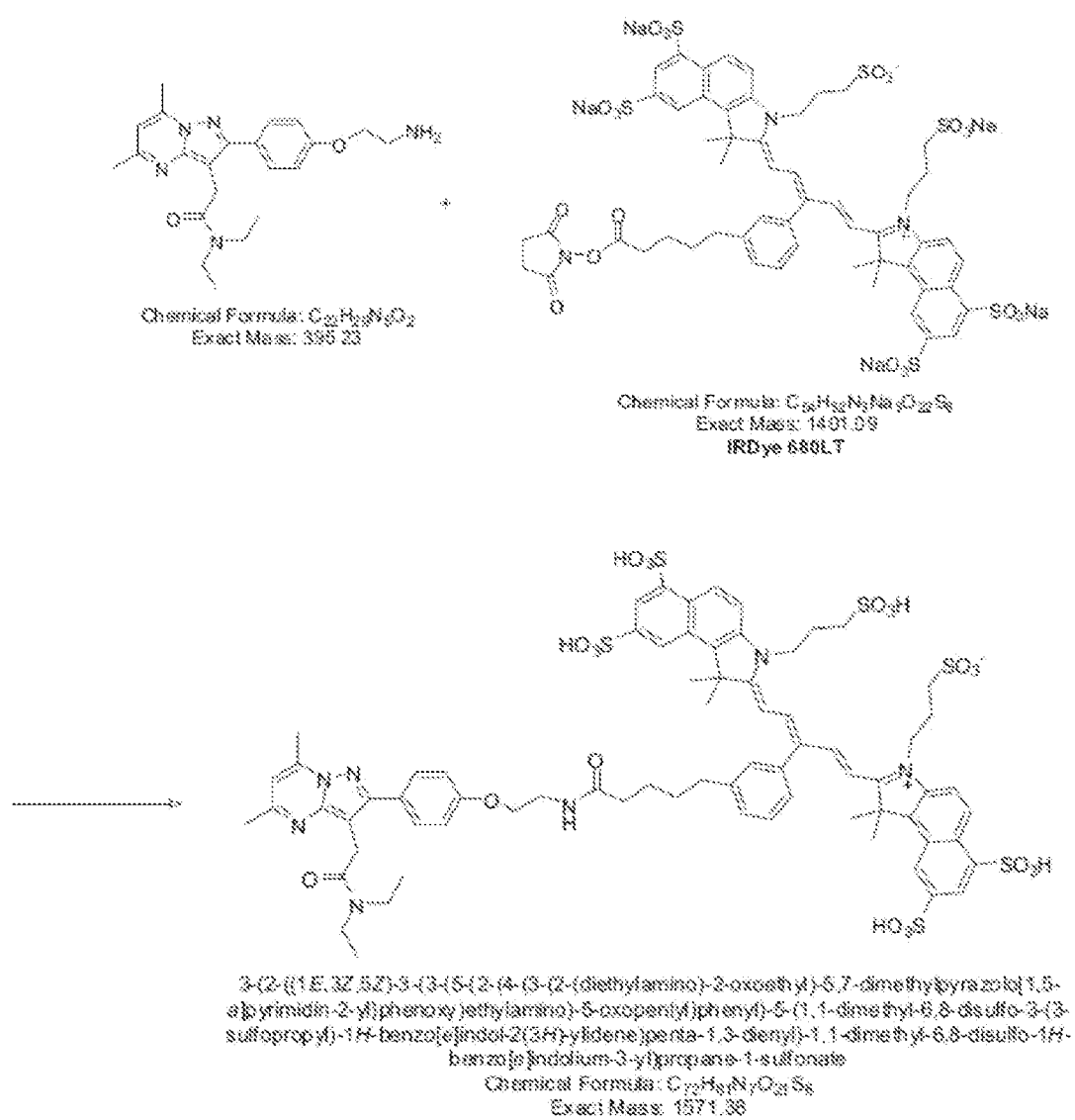
FIG. 1 illustrates the synthetic method for preparing the inventive DPA713 conjugated to IRDye 800CW.

In accordance with an embodiment, the present invention provides a compound of formula I:

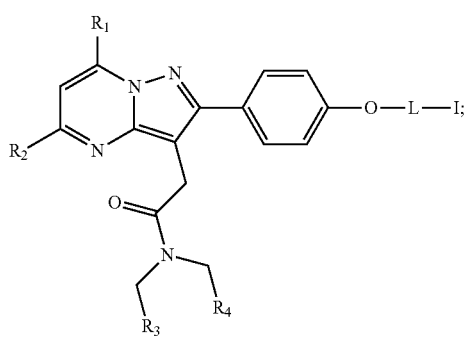

(I)

wherein $R_1$, $R_2$, $R_3$ and $R_4$ independently represent hydroxy, $C_1$ to $C_6$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, an amino acid residue, or a substituted amino acid residue; L is a linker of 1-10 carbon atoms; and I is an imaging agent covalently linked to the linker via an amide linkage.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "cycloalkyl" preferably include a $C_{3-8}$ cycloalkyl (e.g., a cyclopropyl, cyclobutyl, cyclopentyl, cyclohexyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In accordance with an embodiment, the present invention provides a compound of formula I, wherein $R_1$, $R_2$, $R_3$ and $R_4$ are all H.

As used herein, the term "linker, (L)" is a lower alkyl group which is covalently bonded at one end, to an oxygen atom on the phenyl ring of the compound formula I, and covalently bound to an imaging agent (I) on the other end of the linker.

In some embodiments, the linker in the compound of formula I has 2 carbon atoms. In another embodiment, the linker is an ethylamino group.

As used herein, the term "imaging agent" is a fluorescent dye moiety that emits light in the visible or near infrared spectrum. The imaging agent includes any additional atoms or linkers necessary to attach the fluorescent dye moiety to the rest of the compound of formula I, so long as the linker does not interfere with the fluorescence of the dye.

Examples of fluorescent compounds which may form all or part of the structure of the imaging agent of the compound of formula I include carbocyanine, indocarbocyanine, oxacarbocyanine, thiacarbocyanine, merocyanine, polymethine, coumarine, rhodamine, xanthene, fluorescein, and borondipyrromethane (BODIPY) compounds, to name a few.

Examples of fluorescent dye moieties include those described in WO 20089/109832, which is incorporated by reference herein in its entirety.

Specific dyes that can be used with the compound of formula I, which emit in the near infrared spectrum include commercially available compounds Cy5, Cy5.5, and Cy7, available from GE Healthcare; VivoTag-680, VivoTag-5680, and VivoTag-5750, available from VisEn Medical; AlexaFiuor660, AlexaFiuor680, AlexaFiuor700, AlexaFiuor750, and AlexaFiuor790, available from Invitrogen; Dy677, Dy676, Dy682, Dy752, and Dy780, available from Dyonics; DyLight547, and Dylight647, available from Pierce; Hilyte Fluor 647, Hilyte Fluor 680, and Hilyte Fluor 750, available from AnaSpec; IRDye 800CW, IRDye BOORS, and IRDye 700DX, available from Li-Cor; and ADS780WS, ADS830WS, and ADS832WS, available from American Dye Source.

In accordance with some embodiments, the imaging agent linked to compound of formula I is a near infra-red dye, preferably IRDye 800CW or IRDye 680LT.

Embodiments of the present invention also include a process for preparing pharmaceutical products comprising the compounds of formula I. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compounds of formula I. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and ASHP *Handbook on Injectable Drugs*, Trissel, 15th ed., pages 622-630 (2009)).

For purposes of the invention, the amount or dose of the compounds, salts, solvates, or stereoisomers of any one the compounds of formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 1 nmol/kg to about 100 nmol/kg body weight of the subject being treated/day, preferably about 20 nmol/kg to about 80 nmol/kg body weight/day.

As defined herein, in one or more embodiments, "contacting" means that the one or more compounds of the present invention are introduced into a sample having at least one cell or population of cells expressing TSPO, and appropriate enzymes or reagents, in a test tube, flask, tissue culture, chip, array, plate, microplate, capillary, or the like, and incubated at a temperature and time sufficient to permit binding of the at least one compound to the TSPO of the cell. Methods for contacting the samples with the compounds, and other specific binding components are known to those skilled in the art, and may be selected depending on the type of assay protocol to be run. Incubation methods are also standard and are known to those skilled in the art.

In another embodiment, the term "contacting" means that the at least one compound of the present invention is introduced into a subject, and the at least one compounds is allowed to come in contact with the TSPO containing cell or population of cells in vivo.

By "an effective amount" is meant the amount required to identify, diagnose, image, or ameliorate the symptoms of a disease relative in an untreated or treated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "disease" is meant any condition or disorder that damages or interferes with the normal function of a cell, tissue, or organ. Examples of such diseases include: fibrosis, atherosclerosis, coronary artery disease, inflammatory diseases such as rheumatoid arthritis, infectious diseases, vascular disease, cancers or other neoplasias.

The population of cells can be a heterogeneous population comprising the host cell comprising any of the compounds of formula I described, in addition to at least one other cell, e.g., a host cell (e.g., a epithelial cell), which does not comprise any of the nanoparticles, or a cell other than a epithelial cell, e.g., a macrophage, a neutrophil, an erythrocyte, a hepatocyte, a hepatic stellate cell, an endothelial cell, an epithelial cell, a muscle cell, a brain cell, etc. Alternatively, the population of cells can be a substantially homogeneous population, in which the population comprises mainly of host cells (e.g., consisting essentially of) comprising the compounds of formula I.

In some embodiments, the cell or population of cells is selected from the group consisting of leukocytes, tumor cells, CNS cells and cells involved in steroid biogenesis.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In a further embodiment, the compounds of formula I of the present invention can be used in combination with one or more additional therapeutically active agents which are known to be capable of treating conditions or diseases discussed above. For example, the described compounds of formula I of the present invention could be used in combination with one or more known therapeutically active agents, to treat a disease or condition. Non-limiting examples of other therapeutically active agents that can be readily combined in a pharmaceutical composition with the compounds of formula I of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with an embodiment, the present invention provides a method of imaging a cell or population of cells having TSPO activity comprising contacting the cell or population of cells with the compound of formula I, in an effective amount for the compound to bind TSPO and be visualized using known imaging methods. In some embodiments, the imaging methods used are fluorescence detection methods. In other embodiments, the fluorescent imaging uses near infra-red fluorescence detection.

In accordance with an embodiment, the present invention provides a method of imaging a cell or population of cells having TSPO activity in a subject comprising:
a) administering to the subject an effective amount of a compound of formula I or the pharmaceutical composition comprising a compound of formula I; b) allowing sufficient time for the compound of formula I or the pharmaceutical composition comprising the compound to bind the TSPO in the cell or population of cells in the subject; c) exposing the cell or population of cells in the subject to a sufficient amount of infra-red light at the appropriate wavelength; and d) detecting the infra-red fluorescence from the cell or population of cells of the subject which bound the compound of formula I or the pharmaceutical composition comprising the compound.

In accordance with an embodiment, the present invention provides a medicament for imaging a cell or population of cells having TSPO activity in a subject, wherein the medicament comprises an effective amount of a compound of formula I or the pharmaceutical composition comprising a compound of formula I.

In accordance with another embodiment, the present invention provides a method of determining the effectiveness of treatment of a TSPO related disease in a subject comprising: a) administering to the subject an effective amount of a compound of formula I or the pharmaceutical composition comprising a compound of formula I; b) allowing sufficient time for the compound of formula I or the pharmaceutical composition comprising the compound to bind the TSPO in the cell or population of cells in the subject; c) exposing the cell or population of cells in the subject to a sufficient amount of infra-red light at the appropriate wavelength; d) detecting the infra-red fluorescence from the cell or population of cells of the subject which bound the compound of formula I or the pharmaceutical composition comprising the compound; e) administering to the subject at least one therapeutic agent to the subject in a therapeutically effective amount; f) repeating steps a)-d); and g) comparing the amount of fluorescence of step d) before and after step e), wherein when the amount of fluorescence of step d) after step e) is less, than a determination is made that the treatment of the TSPO related disease was effective.

EXAMPLES

Chemicals and solvents obtained from commercial sources were analytical grade or better and used without further purification. Analytical thin-layer chromatography (TLC) was performed using Aldrich aluminum-backed 0.2 mm silica gel plates and visualized by UV light (254 nm) and $I_2$. Flash column chromatography was performed on silica gel (60 Å) from MP Biomedicals. HPLC purification was performed using a Waters (Milford, Mass.) system consisting of two Waters 510 pumps, a Waters 490E variable wavelength UV/Vis detector set at 254 nm, a Waters Luna C18 reverse phase analytical column (4.6 mm×150 mm) with $H_2O/CH_3CN/TFA$ solvent systems, and Win Flow (LabLogic) chromatography software. $^1H$ NMR was recorded on a Bruker (Billerica, Mass.) Ultrashield™ 400 MHz spectrometer. ESI mass spectra were obtained with a Bruker Daltonics Esquire 300 plus spectrometer.

Synthesis of 2-(2-(4-(2-aminoethoxy)phenyl)-5,7-dimethylpyrazolo[1,5-a]pyrimidin-3-yl)-N,N-diethylacetamide (Compound 1). To 100 mg of desmethyl DPA 713 in 5 mL of DMF was added 1 g of $K_2CO_3$. After stirring at room temperature for 30 minutes, Boc-2-aminoethylbromide (mg, 1.5 eq) was added. The reaction mixture was stirred overnight at 80° C. and was then diluted with 20 ml of water and extracted with chloroform (2×20 ml). The combined organic layer was washed with brine (1×10 ml), dried over $MgSO_4$ and purified with flash chromatography using 40:1 dichloromethane:Methanol. The fractions that contains intermediate tert-butyl 2-(4-(3-(2-(diethylamino)-2-oxoethyl)-5,7-dimethylpyrazolo[1,5-a]pyrimidin-2-yl)phenoxy) ethylcarbamate was collected and vacuum dried and dissolve in 0.5 ml of TFA. After stirring for 1 hour, excess TFA was evaporated and residue was purified by reverse phase HPLC. HPLC conditions used were 75% $H_2O$/25% $CH_3CN$/0.1% TFA at flow rate of 3 ml/min on an Alltech semiprep C18 column. Rention time for the desired product 2-(2-(4-(2-aminoethoxy)phenyl)-5,7-dimethylpyrazolo[1,5-a]pyrimidin-3-yl)-N,N-diethylacetamide is 13.6 minutes. $^1$H NMR ($CD_3OD$, 400 Mhz δ 1.10 (t, 3H, J=6.8 Hz), 1.23 (t, 3H, J=6.4 Hz), 2.56 (s, 3H), 2.75 (s, 3H), 3.30-3.40 (m, 4H), 3.53-3.58 (m, 2H), 3.97 (s, 2H), 4.27-4.29 (m, 2H), 6.80 (s, 1H), 7.11 (d, 2H, J=8 Hz), 7.69 (d, 2H, J=8 Hz). ESI MS m/z: [M+H]+. $C_{22}H_{29}N_5O_2$: calculated 396.2. found 396.1.

Synthesis of 1-(6-(2-(4-(3-(2-(diethylamino)-2-oxoethyl)-5,7-dimethylpyrazolo[1,5-a]pyrimidin-2-yl)phenoxy)ethylamino)-6-oxohexyl)-2-((E)-2-((E)-3-((E)-2-(3,3-dimethyl-5-sulfo-1-(4-sulfobutyl)indolin-2-ylidene)ethylidene)-2-(4-sulfophenoxyl)cyclohex-1-enyl)vinyl)-3,3-dimethyl-3H-indolium-5-sulfonate (Compound 2). To a solution of 1 (0.15 mg, μmol) in DMSO (0.1 mL) was added triethyl amine (5 μl), followed by the NHS ester of IRDye 800CW (0.5 mg, μmol). After stirring for 2 hours at room temperature, the reaction mixture was purified by HPLC; HPLC conditions used were a linear gradient from 100% $H_2O$/0% CH/0.1% TFA to 0% $H_2O$/100% $CH_3CN$/0.1% TFA for 45 minutes at a flow rate of 1 ml/min using a Waters Luna C18 analytical column. Retention time is 21.6 minutes. The desired fraction of compound 2 was collected and lypholized to give 0.2 mg of 2(%). ESI-Mass calculated for $C_{68}H_{81}N_7O_{16}S_4$ [M]+1379.4. found 690.2 [M+H]2+, 1379.4[M]+.

Synthesis of 3-(2-((1E,3Z,5Z)-3-(3-(5-(2-(4-(3-(2-(diethylamino)-2-oxoethyl)-5,7-dimethylpyrazolo[1,5-a]pyrimidin-2-yl)phenoxy)ethylamino)-5-oxopentyl)phenyl)-5-(1,1-dimethyl-6,8-disulfo-3-(3-sulfopropyl)-1Hbenzo[e]indol-2(3H)-ylidene)penta-1,3-dienyl)-1,1-dimethyl-6,8-disulfo-1H-benzo[e]indolium-3-yl)propane-1-sulfonate (Compound 3). To a solution of 1 (0.15 mg, μmol) in DMSO (0.1 mL) was added triethyl amine (5 μl), followed by the NHS ester of IRDye 680LT (0.5 mg, μmol). After stirring for 2 hours at room temperature, the reaction mixture was purified by HPLC; the HPLC condition used was a linear gradient from 100% $H_2O$/0% $CH_3CN$/0.1% TFA to 0% $H_2O$/100% $CH_3CN$/0.1% TFA in 45 minutes at a flow rate of 1 ml/min in using a Waters Luna C18 analytical column. The retention time was 24.5 minutes. The desired fraction of compound was collected and lypholized to give 0.2 mg of 2(%). ESI-Mass calculated for: $C_{72}H_{81}N_7O_{21}S_6$ [M. found [M+H] 2+786.2, [M]+1571.6.

In vitro J774 murine macrophage uptake studies. The immortalized J774 murine macrophage-like cell line was cultured in RPMI1640+20% FBS+1% penicillin+ streptomycin media in 8-well chamber slides (Fisher Scientific) to approximately 80% confluence. The cells were then stimulated with 1 ng/mL of LPS (Sigma, E. coli 055:B5) for 24 hours prior to addition of the probes of the present invention to 40 nM final concentration. Wells that received blocking compounds contained either 1 μM (R,S)-PK11195 (Sigma) or 1 μM DPA-713 conjugated to the IR dye. The cells were exposed to the fluorescent probes and blocking compounds for either 1 hour or 24 hours prior to exposing to 1 ng/mL of Hoechst 33342 dye (Invitrogen), followed by washing twice briefly with PBS, pH 7.5. The chambers were then removed and the slide mounted with Dako Cytomation aqueous mounting media and a glass coverslip. The cells were visualized using a Nikon 80i upright epifluorescence microscope equipped with a Nikon DS-QilMc darkfield CCD camera and processed using Nikon Image Software on an adjacent workstation. The dyes were excited using either a Nikon Intensilight C-HGFI lamp (IRDye680 and Hoechst) or a Sutter Instruments Co. (Novato, Calif.) LB/LB-30 xenon lamp (IRDye800).

Figure 3:
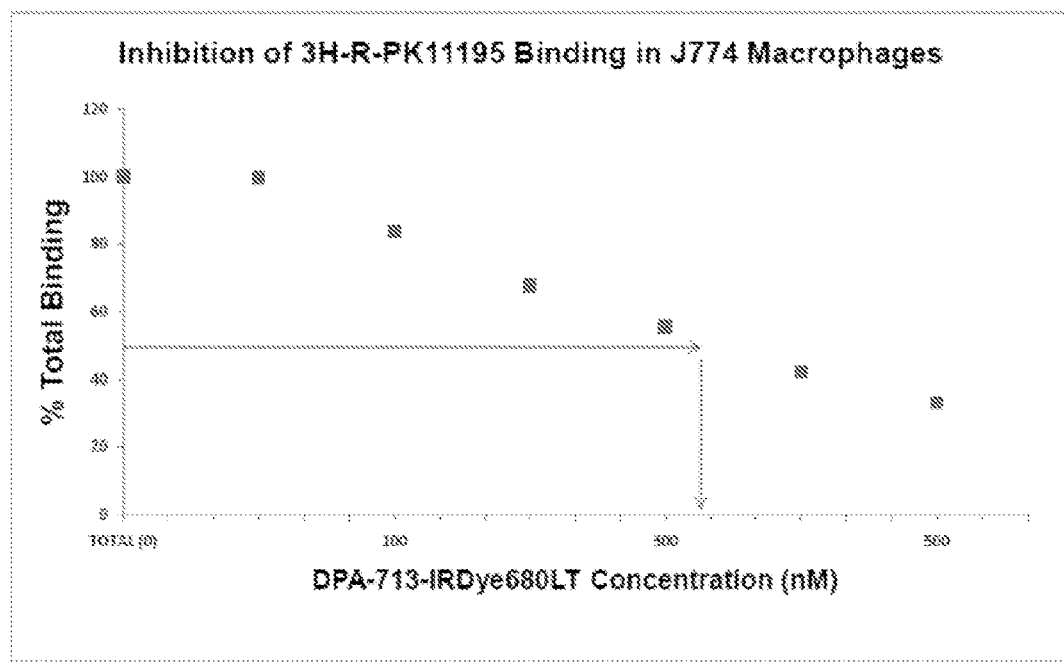
FIG. 3 is a graph showing the IC$_{50}$ for inhibition of 3H-R-PK11195 binding in J774 macrophages by DPA713-IRDye680LT (nM). The IC$_{50}$ was approximately 325 nM.
Figure 4:
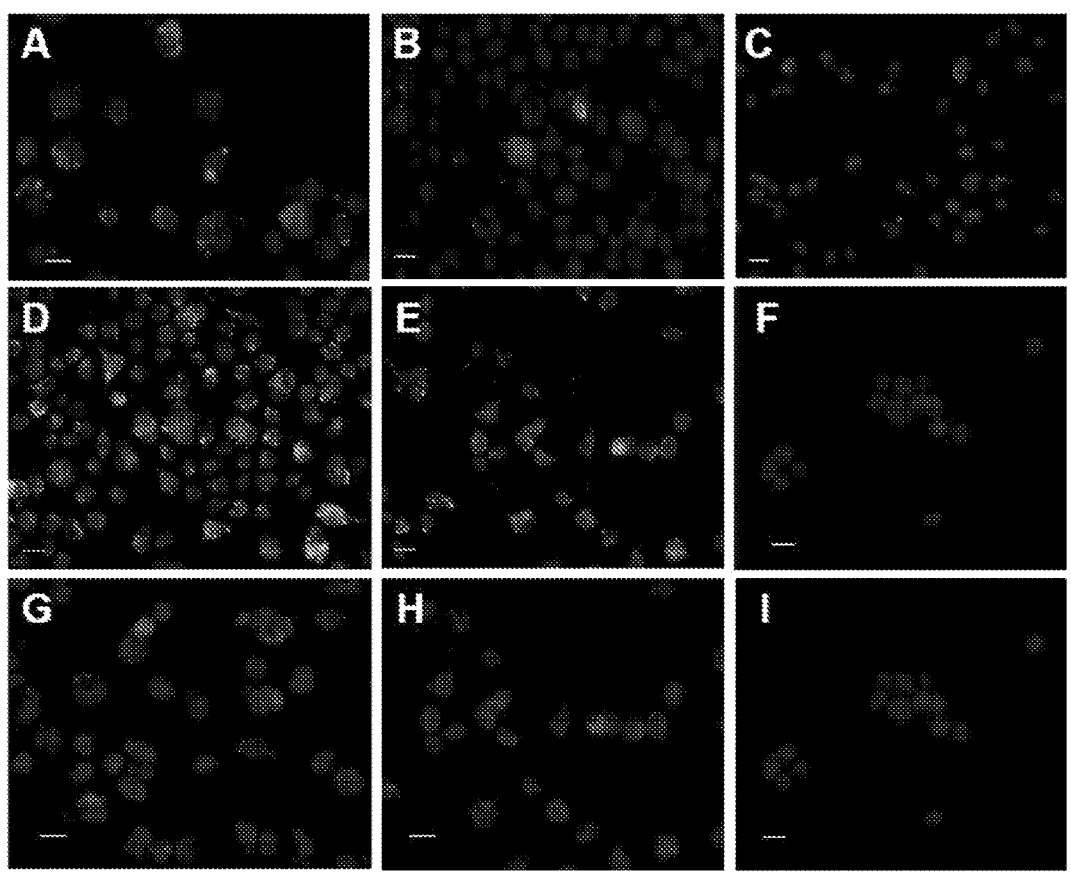
FIG. 4 is a series of photomicrographs (A-I) of J774 macrophages that were cultured in 8 well chamber slides to 80% confluence. LPS was then added to each well for 24 hours to stimulate the cells. Both DPA-713-IRDye680LT and DPA-713-IRDye800CW (40 nM each) were then added to each well with or without an excess of competing unlabeled PK11195 or DPA-713. The cells were returned to the incubator for either 1 hour or 24 hours. The solutions were then removed, the nuclei were labeled with Hoechst 33342 and the cells were briefly washed before mounting and viewing under a fluorescence microscope.

The $IC_{50}$ value determination was done by using a fixed number of live murine J774 macrophage-like cells and incubating increasing concentrations of DPA-713-IRDye against a fixed concentration of [$^3$H]PK11195. All reactions and washes (50 mM Tris, pH 7.4) are done using a Brandell Cell Harvester and the cells are counted in a scintillation counter with scintillent at the end. The cpm for each group is then plotted against the log of DPA-713-IRDye concentration and the data fitted to a sigmoidal curve. The 50% inhibition of [$^3$H]PK11195 binding is then determined and reported as the $IC_{50}$ (FIG. 3).

Cell lines and Tumor Models. Generation of MDA-MD-231-LMD-PSMA cells. LV-PSMA is a VSV-G pseudotyped lentivirus encoding PSMA which was packaged in 293T cells. LMD-PSMA cells were generated in-house by repetitive lentiviral transduction of a cell line isolated from a lung metastasis derived MDA-MB-231 xenograft in a female NOD-SCID mouse. PSMA expression was evaluated by western blot analysis with 7E11-05 (1:200 dilution). No differences in growth of morphology were observed in cell culture between the parental LMD cells and PSMA transduced LMD-PSMA cells. Six-to-eight week old female NOD SCID mice were injected subcutaneously with 5×10$^6$ MDA-MB-231-LMD (a lung metastasis-derived subline of parental MDA-MB-231 behind the right forearm and 5×10$^6$ MDA-MB-231-LMD-PSMA (the same cell line with Prostate Specific Membrane Antigen (PSMA) stably knocked in via lentiviral vector) injected behind the right forearm. The xenografts were allowed to grow until the PSMA xenograft was at least 3 mm in diameter while the -LMD xenograft had reached 6-8 mm in diameter.

Prostate lines PC-3 PIP (PSMA stable transfected) and PC-3 flu (empty vector transfected) cells were originally a gift from Warren B. Heston (Cleveland Clinic Foundation). PC-3 is androgen insensitive and constituitively expresses TSPO. LNCaP cells were originally procured from the ATCC (Manassas, Va.) and do not express TSPO when grown as xenografts within intact male mice. Intact male athymic nude mice were inoculated subcutaneously with 2×10$^6$ PC-3 PIP cells behind the right forearm and 2×10$^6$ PC-3 flu cells behind the left forearm and were allowed to grow for 14 days until they reached 1 cm in longest diameter. Mice bearing LNCaP xenografts were inoculated with 5×10$^6$ cells in Matrigel (1:1, vol:vol) (Becton Dickenson, Franklin Lakes, N.J.) and were allowed to grow for a year before they reached 1 cm in diameter. The mice were then used in imaging experiments as described below.

Serial in vivo NIRF imaging in TSPO+MDA-MB-231 LMD±PSMA and PC-3 PIP and -flu tumor xenograft bearing mice. MDA-MB-231 LMD lines: one mouse was imaged serially at 1 hour post-tracers, 4 hours, 8 hours and 24 hours post-tracers using a Pearl Impulse Imager (LI-COR Biosciences) with dedicated 710 and 800 nm emission filters. All images were scaled to the same maximum using the manufacturer's software to facilitate direct comparison of all timepoints. The remaining mice were sacrificed by cervical dislocation along the indicated timepoints, they were imaged ex vivo with their body cavity exposed and their tissues were then harvested and frozen over dry ice for cryosectioning followed by ex vivo microscopy described above.

PC-3 PIP and -flu xenograft bearing mice. Two mice bearing similar pairs of 1 cm tumors were injected intraperitoneally with either 8 nmol of the inventive probe DPA-713-IRDye680LT or 8 nmol of the inventive probeDPA-713-IRDye680LT+20 mg/kg of unlabeled DPA-713 competitor. The mice were anesthetized with isoflurane gas (2% in oxygen) and imaged at 1 hour and 24 hours post-injection using the Pearl Impulse imager using the 680 absorption/710 emission channels (DPA-713-IRDye680LT). PIP/flu and LNCaP-bearing mice were imaged using the inventive probe DPA-713-IRDye800CW at 1 hour post-injection using a Perkin Elmer IVIS 200 instrument set to absorb at 790 nm and emit at 810 nm. Images were visualized and processed using the manufacturer's Living Image software.

Ex vivo DPA-713-IRDye680LT microscopy. The mice used in the in vivo NIRF studies (PC-3 analog xenografts and MDA-MB-231 analog xenografts) were sacrificed at the end of their studies and their tumors were collected and frozen on dry ice for cryosectioning to 20 microns on charged glass slides (VWR). The sections were then probed with both anti-TSPO Ab (Novus Biologicals NBP1-45769, 1:70) labeled directly with Lissamine sulfonyl chloride (Aldrich) according to the known method and anti-CD68 Ab (Abcam ab53444, 1:40) and lastly with Hoechst 33342 (Invitrogen, 1 ng/mL). Both antibodies were added simultaneously in a 10% FBS in PBS solution applied directly to the freshly thawed sections and allowed to sit at room temperature for 1 hour. The sections were washed twice at room temperature for 5 minutes each with PBS prior to the addition of sheep-anti-rat-FITC (Abcam ab6848-1, 1:250) in PBS at room temperature for 30 minutes. The secondary antibody solution was removed and the slides were bathed in Hoechst solution (PBS) for 1.5 minutes at room temperature before being washed twice as before with PBS. The slides were then mounted in Dako Cytomation aqueous mounting media with a glass coverslip and viewed 30 minutes later using a Nikon 80i upright epifluorescence microscope equipped with a Nikon DS-QilMc darkfield CCD camera and excited by a Nikon Intensilight C-HGFI lamp. All images are recorded and processed using Nikon Imaging Software Elements.

Example 1

Figure 2:
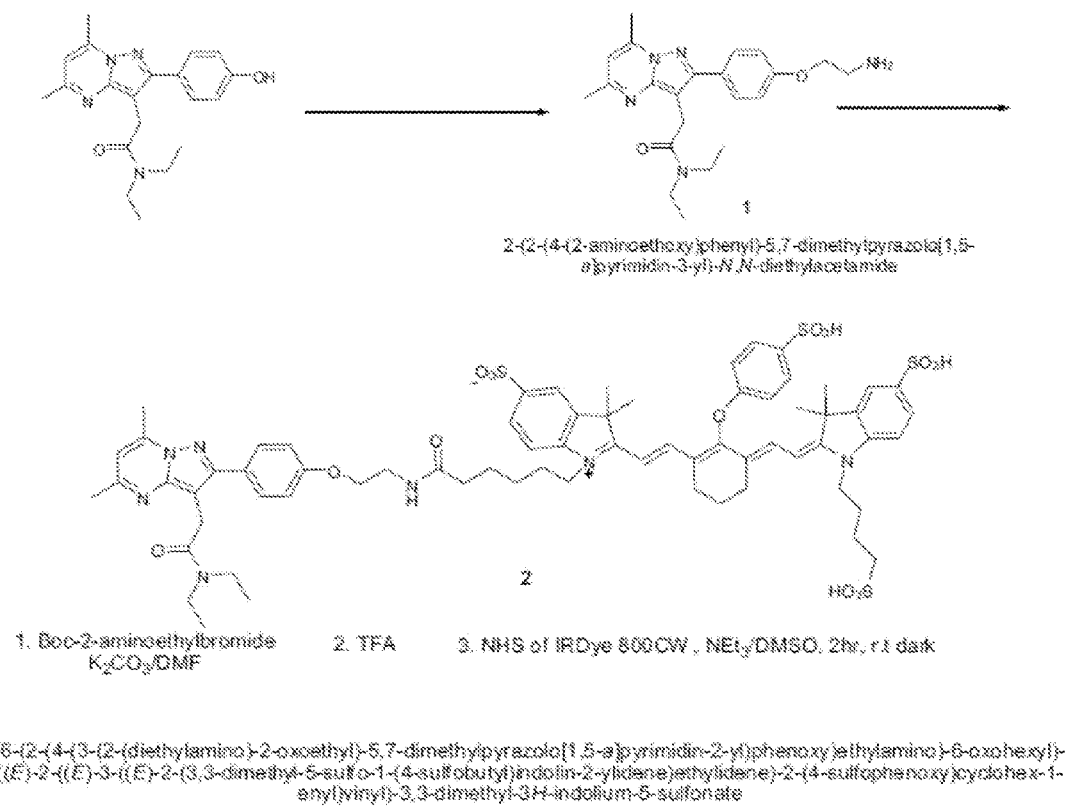
FIG. 2 illustrates the synthetic method for preparing the inventive DPA713 conjugated to IRDye 650LT.

Two of the inventive DPA-713 based near-infrared fluorescent imaging probes were synthesized from desmethyl DPA-713 (FIGS. 1 and 2). Chemicals and solvents obtained from commercial sources were analytical grade or better and used without further purification. Iodine-125 ($^{125}$I) was obtained as a 0.1 N solution of NaOH (high concentration) from MP iomedicals (Solon, Ohio). Analytical thin-layer chromatography (TLC) was performed using Aldrich aluminum-backed 0.2 mm silica gel plates and visualized by UV light (254 nm) and 12. Flash column chromatography was performed on silica gel (60 AA 0) from MP Biomedicals. Radio-HPLC purification was performed using a Waters (Milford, Mass.) system consisting of two Waters 510 pumps, a Waters 490E variable wavelength UV/Vis detector set at 254 nm, a BioScan FlowCount radioactivity detector, a Waters radial-PAK C18 reverse phase analytical column (8×100 mm) with $H_2O/CH_3CN/TFA$ solvent systems, and Win Flow (LabLogic) chromatography software. $^1H$ NMR was recorded on a Bruker (Billerica, Mass.) Ultrashield™ 400 MHz spectrometer. ESI mass spectra were obtained with a Bruker Daltonics Esquire 300 plus spectrometer.

Synthesis of 2-(2-(4-(2-aminoethoxyl)phenyl)-5,7-dimethylpyrazolo[1,5-a]pyrimidin-3-yl)-N,N-diethylacetamide. To 100 mg of desmethyl DPA 713 in 5 mL of DMF was added 1 g of $K_2CO_3$. After stirring at room temperature for 30 minutes, Boc-2-aminoethylbromide (mg, 1.5 eq) was added. The reaction mixture was stirred overnight and was then diluted with 20 ml of water and extracted with chloroform (2×20 ml). The combined organic layer was washed with brine (1×10 ml), dried over $MgSO_4$ and purified with flash chromatography using 40:1 dichloromethane:Methanol. The fractions that contains intermediate tert-butyl 2-(4-(3-(2-(diethylamino)-2-oxoethyl)-5,7-dimethylpyrazolo[1,5-a]pyrimidin-2-yl)phenoxy)ethylcarbamate was collected and vacuum dried and dissolve in 0.5 ml of TFA. After stirring for 1 hour, excess TFA was evaporated and residue was purified by reverse phase HPLC. HPLC condition used were 75% $H_2O$/25% $CH_3CN$/0.1% TFA at flow rate of 3 mL/minute on an Alltech semiprep C18 column. Retention time for the desired product 2-(2-(4-(2-aminoethoxyl)phenyl)-5,7-dimethylpyrazolo[1,5-a]pyrimidin-3-yl)-N,N-diethylacetamide is 13.6 minutes. $^1H$ NMR (CD3OD, 400 MHz) δ 1.10 (t, 3H, J=6.8 Hz), 1.23 (t, 3H, J=6.4 Hz), 2.56 (s, 3H), 2.75 (s, 3H), 3.30-3.40 (m, 4H), 3.53-3.58 (m, 2H), 3.97 (s, 2H), 4.27-4.29 (m, 2H), 6.80 (s, 1H), 7.11 (d, 2H, J=8 Hz), 7.69 (d, 2H, J=8 Hz). ESI MS m/z: [M+H]+. C22H29N5O2: calculated 396.2. found 396.1.

Synthesis of 1-(6-(2-(4-(3-(2-(diethylamino)-2-oxoethyl)-5,7-dimethylpyrazolo[1,5-a]pyrimidin-2-yl)phenoxy)ethyl-amino)-6-oxohexyl)-2-((E)-2-((E)-3-((E)-2-(3,3-dimethyl-5-sulfo-1-(4-sulfobutyl)indolin-2-ylidene)ethylidene)-2-(4-sulfophenoxyl)cyclohex-1-enyl)vinyl)-3,3-dimethyl-3H-indolium-5-sulfonate. To a solution of (0.15 mg, µmol) in DMSO (0.1 mL) was added triethyl amine (2 µl), followed by the NHS ester of IRDye 800CW (0.5 mg, µmol). After stirring for 2 hours at room temperature, the reaction mixture was purified by HPLC 150×4.6 mm; retention time, min, mobile phase, A=0.1% TFA in $H_2O$, B=0.1% TFA in $CH_3CN$; gradient, 0 min=0% B, 5 min=0% B, 45 min=100% B; flow rate, 1 mL/min) to afford 0.2 mg (72%) of 3. ESI-Mass calcd for: $C_{68}H_{81}N_7O_{16}S_4$ [M]+1379.4. found 690.2 [M+H]2+, 1379.4[M]+.

Example 2

J774 Cell Uptake Studies. J774 macrophages were cultured in 8 well chamber slides to 80% confluence. LPS was then added to each well for 24 hours to stimulate the cells. Both DPA-713-IRDye680LT and DPA-713-IRDye800CW (40 nM each) were then added to each well with or without an excess of competing unlabeled PK11195 or DPA-713. The cells were returned to the incubator for either 1 hour or 24 hours. The solutions were then removed, the nuclei were labeled with Hoechst 33342 and the cells were briefly washed before mounting and viewing under a fluorescence microscope. FIG. 4A-F shows the uptake of the IRDye680LT analog at 1 and 24 hours of incubation, while panels G-I shows the uptake of the IRDye800CW analog after 24 hours of incubation. There was almost no observable signal from the IRDye800CW analog after 1 hour of incubation, likely due to the inherently lower sensitivity of the detector at this wavelength. The tracer localization for both analogs is perinuclear and granular in appearance and is consistent with the gross distribution pattern of TSPO expression in other mononuclear cell-derived lines. Co-administration of 1 µM unlabeled TSPO-specific ligand (R,S)-PK11195 along with 40 nM DPA-713-IRDye680LT resulted in widespread although incomplete blocking of tracer uptake at 1 hour (panel B). Co-administration of 1 µM unlabeled DPA-713 along with the same concentration of tracer resulted in partial but incomplete blocking of tracer uptake (panel C) at 1 hour. After 24 hours of incubation with both tracer and blocking agents, (R,S)-PK11195 no longer blocked DPA-713-IRDye680LT uptake (panels E, H) although the presence of 1 µM unlabeled DPA-713 virtually eliminated binding of both analogs (panels F, I).

Example 3

Figure 5:
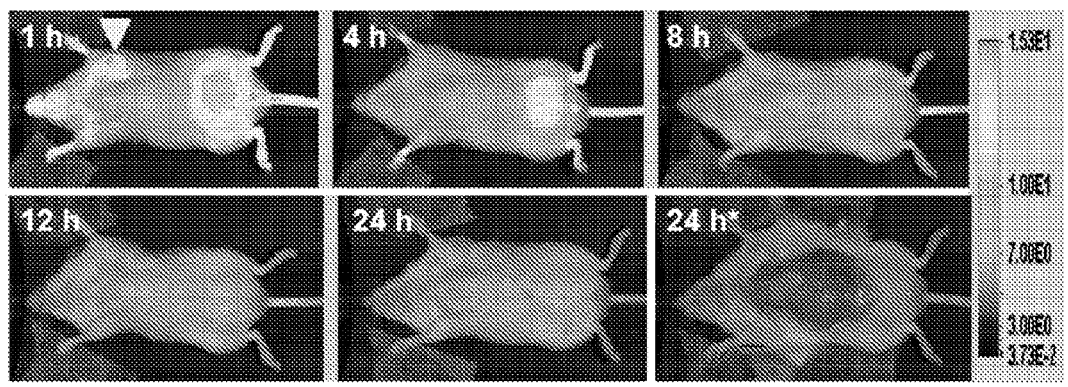
FIG. 5 shows NIRF imaging of MDA-MB-231 breast xenografts (arrowhead) can be imaged in vivo at 1 hour post DPA-713-IRDye680 using NIRF imaging or through 24 hour post-tracer during survival surgery or at necropsy.

In vivo NIRF imaging of DPA-713-IRDye680LT in TSPO+MDA-MB-231 breast cancer and TSPO+PC-3 prostate cancer xenografts. NOD-SCID mice were inoculated subcutaneously with a parental MDA-MB-231 and a stably transfected MDA-MB-231-PSMA (expressing prostate-specific membrane antigen) cell line, both of which constituitively express TSPO. In our experience, cell lines ectopically expressing PSMA harbor more macrophages and are more vascular than their parental lines. This difference in macrophage density was the target for comparison between this otherwise isogenic tumor line. The mice were injected intraperitoneally with 6 nmol of DPA-713-IRDye680LT when the xenografts had reached ≥4 mm in diameter. The mice were imaged after 1, 4, 8, 12 and 24 hours post-probe injection, followed by ex vivo imaging of the tumors at 24 hours. FIG. 5 shows the in vivo uptake in a mouse bearing an 8 mm PSMA+ xenograft on one side (left arrowhead) and a 3 mm parental xenograft on the other. Probe uptake in the larger xenograft is visible 1 hour following peritoneal injection and continues through 24 hours after injection while background uptake clears. The smaller parental xenograft displays no observable uptake until the fur and skin are removed at 24 hours post-injection (24 h*). The larger, PSMA expressing xenograft is visibly brighter than the smaller parental tumor.

Example 4

Figure 8:
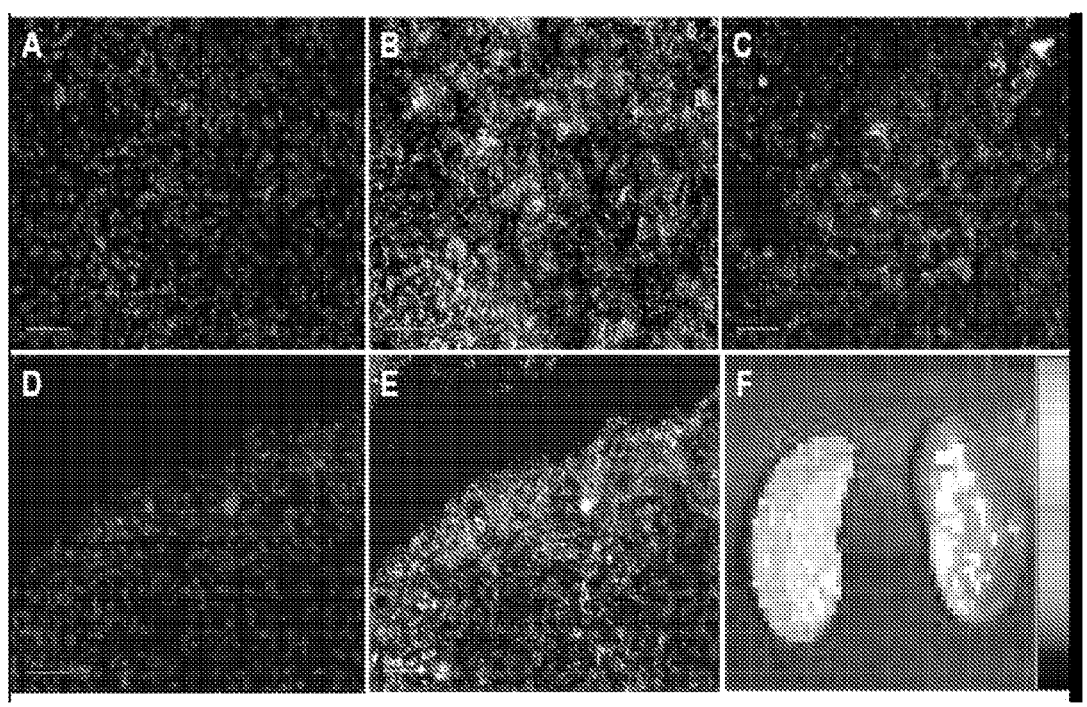
FIG. 8 is a series of photomicrographs showing ex vivo fluorescence microscopy of DPA-713-IRDye680LT in PC-3 PIP and PC-3 flu xenografts at 24 hours post-injection. PC-3 PIPs accumulate more DPA-713-IRDye680LT that PC-3 flu xenografts due to higher density of macrophage infiltration. DPA-713-IRDye680LT accumulation is blocked by co-injection with 20 mg/kg of unlabeled DPA-713. A & B. PIP tumor DPA-713-IRDye680LT only; C. PIP tumor+DPA-713-IRDye680 LT+20 mg/kg DPA-713; D & E. Flu tumor, DPA-713-IRDye 680LT only; F. Laterally bisected kidneys showing tracer only (left) and tracer+20 mg/kg DPA-713 Bar=100 microns.

Prostate tumors that have become androgen insensitive constituitively express TSPO, including the PC-3 cell line. Athymic nude mice bearing two subcutaneous xenografts each consisting of one PC-3 PIP (PSMA+ stable transfected, macrophage and vasculature enriched) and PC-3 flu (PC-3 transfected with empty vector) were injected intraperitoneally with 8 nmol of DPA-713-IRDye680LT when the tumors reached 4-8 mm in diameter. One mouse was injected with tracer only and one mouse received tracer co-injected with 20 mg/kg of unlabeled DPA-713. The mice were imaged in vivo at 1 hour post-injection and again at 24 hours post-injection. FIG. 8 shows the distribution of fluorescent signal at these two time points. At 1 hour post-injection, only the macrophage enriched PC-3 PIP tumor is clearly visible (arrowhead) in both dorsal and ventral views. Neither tumor takes up the fluorescent probe when unlabeled DPA-713 is co-administered. By 24 hours post-injection, fluorescence intensity is now distributed at the periphery of both tumors in the tracer-only mouse and is strongly retained by TSPO+ kidneys. The mouse co-injected with unlabeled DPA-713 displays neither tumor nor kidney uptake. Additionally, the unbound probe has cleared from the peritoneal space.

Example 5

Figure 6:
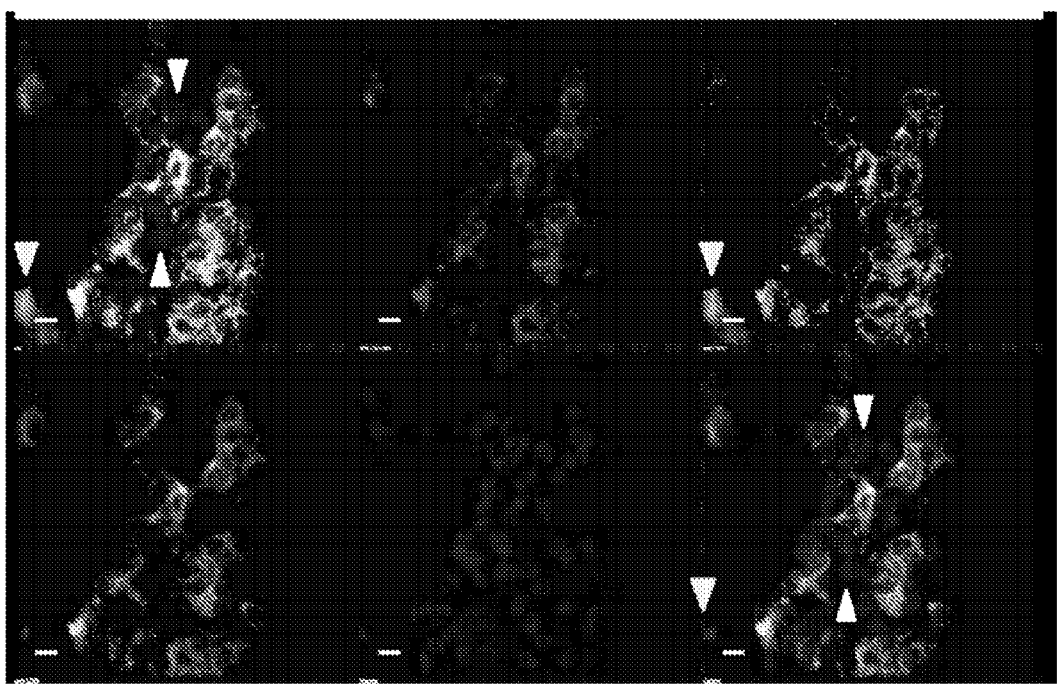
FIG. 6 is a series of photomicrographs of ex vivo fluorescence microscopy of DPA-713-IRDye680LT in MDA-MB-231 xenografts at 24 hours post-injection. DPA-713-IRDye680LT is sequestered within CD68+ macrophages at 24 hours post-injection.
Figure 7:
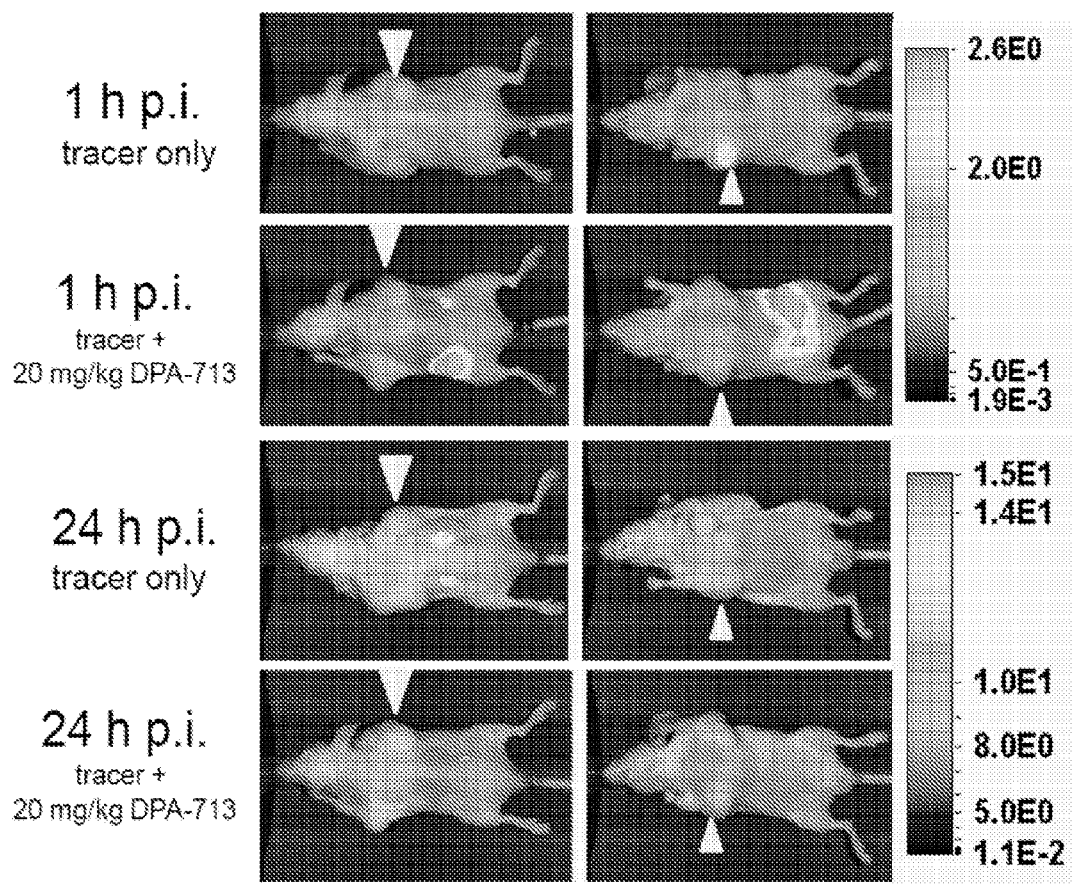
FIG. 7 depicts imaging of athymic nude mice bearing two subcutaneous xenografts each consisting of one PC-3 PIP (PSMA+ stable transfected, macrophage and vasculature enriched) and PC-3 flu (PC-3 transfected with empty vector) were injected intraperitoneally with 8 nmol of DPA-713-IRDye680LT when the tumors reached 4-8 mm in diameter. One mouse was injected with tracer only and one mouse received tracer co-injected with 20 mg/kg of unlabeled DPA-713. The mice were imaged in vivo at 1 hour post-injection and again at 24 hours post-injection.

Ex vivo microscopy. Both MDA-MB-231 LMD xenografts were removed, frozen and sectioned onto charged glass for analysis of cell-specific localization of the inventive DPA-713-IRDye680LT probe at 24 hours post-injection. The sections were subsequently probed with antibodies to delineate the presence of CD68 expressing mononuclear cells, which are known to upregulate TSPO expression when activated, as well as an antibody to delineate all TSPO expression within the tissue. FIG. 6 demonstrates that at 24 hours post-injection, DPA-713-IRDye680LT is selectively retained by CD68-expressing macrophages, despite the presence of TSPO-expressing epithelial MDA-MB-231 cells (data not shown). Cells negative for CD68 and TSPO expression are also devoid of DPA-713-IRDye680LT. This ex vivo data supports the results shown in FIG. 4, which demonstrate that TSPO-specific uptake of DPA-713-IRDye680LT is blocked at early (1 hour) timepoints by TSPO-specific ligand PK11195 but not at late (24 hour) time points. Autoblockade is effective at both early and late timepoints, demonstrating specificity of binding as well as indicating TSPO-independent trapping at late timepoints. This heterogeneity in TSPO-targeted probe binding has been reported by others although the identity of any other target(s) has not been elucidated.

Example 6

Figure 9:
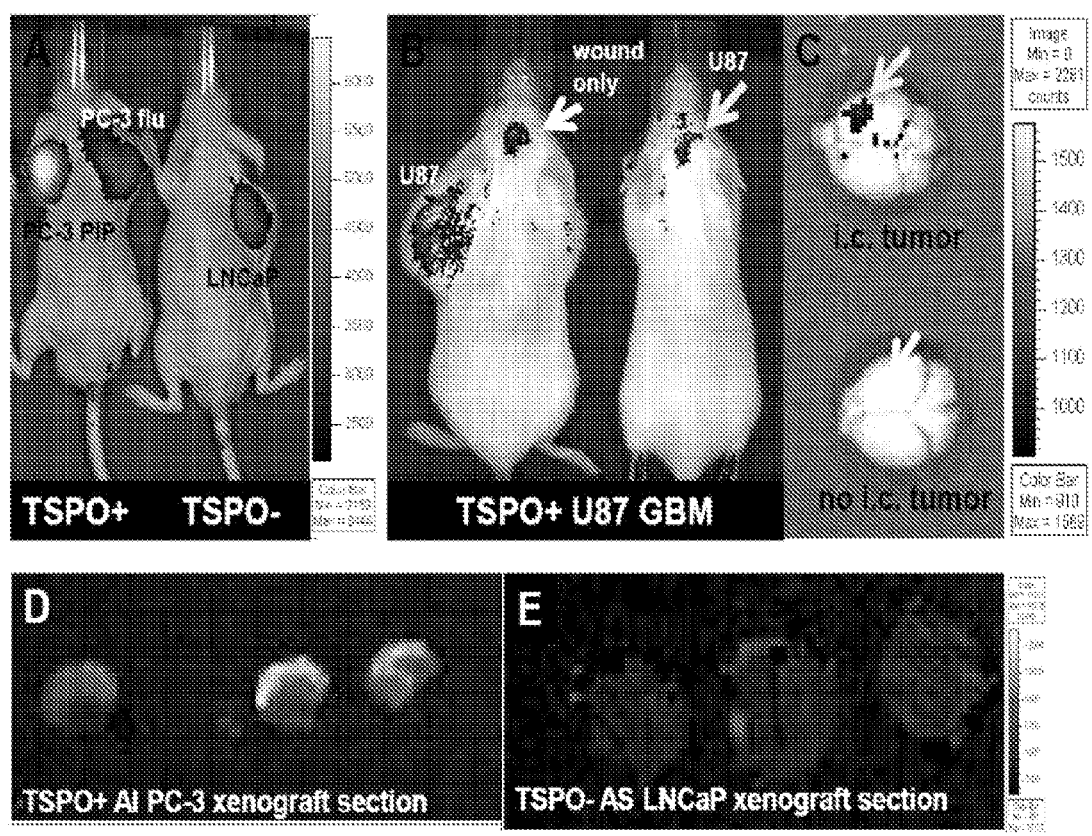
FIG. 9 is a series of NIRF image showing in vivo, ex vivo and in vitro binding of DPA-713-IRDye800CW to androgen sensitive (TSPO−) LNCaP, androgen insensitive (TSPO+) PC-3 prostate xenografts and TSPO+ subcutaneous and orthotopic U87 GBM xenografts.

FIG. 9 depicts a series of NIRF image showing in vivo, ex vivo and in vitro binding of DPA-713-IRDye800CW to androgen sensitive (TSPO−) LNCaP (9E), androgen insensitive (TSPO+) PC-3 prostate xenografts and TSPO+ subcutaneous and orthotopic U87 GBM xenografts. The figures show the ex vivo accumulation of DPA-713-IRDye680LT within CD68+(green) macrophages in a PSMA+ prostate tumor xenograft (9A & 9B), DPA-IRDye blocking by co-administration of 20 mg/kg unlabeled DPA-713 (9C) and less probe accumulation in less-macrophage containing PSMA− PC-3 tumor xenografts (9D). Thus, the inventive compound, DPA-713-IRDye680LT, after 24 hours of in vivo biodistribution, accumulated specifically within CD68+ macrophages within prostate tumor xenografts despite constitutive epithelial TSPO expression by both xenograft types (confined to macrophages at 24 hours).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I:

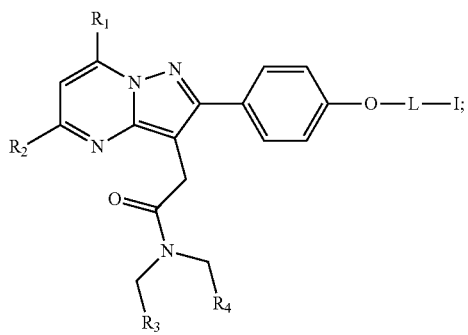

(I)

wherein $R_1$, $R_2$, $R_3$ and $R_4$ independently represent hydroxy$C_1$ to $C_{10}$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, an amino acid residue, or a substituted amino acid residue;

L is a linker of 1-10 carbon atoms; and

I is an imaging agent covalently linked to the linker via an amide linkage.

2. The compound of claim 1, wherein $R_1$, $R_2$, $R_3$ and $R_4$ are all H.

3. The compound of claim 1, wherein L is a linker of 2 carbon atoms.

4. The compound of claim 1, wherein I is a near infra-red dye.

5. The compound of claim 1, wherein the near infra-red dye is IRDye 800CW or IRDye 680LT.

6. A pharmaceutical composition comprising an effective amount of a compound of claim 1, and a pharmaceutically acceptable carrier.

7. A method of imaging a cell or population of cells having translocator protein (TSPO) activity comprising contacting the cell or population of cells with the compound of claim 1, in an effective amount for the compound to bind TSPO and be visualized with infra-red light.

8. The method of claim 7, wherein the cell or population of cells is selected from the group consisting of leukocytes, tumor cells, CNS cells and cells involved in steroidbiogenesis.

9. A method of imaging a cell or population of cells having translocator protein (TSPO) activity in a subject comprising:
  a) administering to the subject an effective amount of the compound of claim 1;
  b) allowing sufficient time for the compound of claim 1 to bind the TSPO in the cell or population of cells in the subject;
  c) exposing the cell or population of cells in the subject to a sufficient amount of infra-red light at the appropriate wavelength; and
  d) detecting the infra-red fluorescence from the cell or population of cells of the subject which bound the compound of claim 1.

10. The method of claim 9, wherein the cells or population of cells in the subject are leukocytes, tumor cells, CNS cells and cells involved in steroid biogenesis.

11. The method of claim 9, wherein the subject is a mammal.

12. The method of claim 9, wherein the subject is human.

* * * * *